(12) United States Patent
Fukunishi et al.

(10) Patent No.: US 9,133,090 B2
(45) Date of Patent: Sep. 15, 2015

(54) DIVINYL-ETHER COMPOUND AND MANUFACTURING METHOD THEREFOR

(75) Inventors: Youichi Fukunishi, Kanagawa (JP); Masahiro Murotani, Kanagawa (JP)

(73) Assignee: NIPPON CARBIDE INDUSTRIES CO., LTD., Tokyo (JP)

( * ) Notice: Subject to any disclaimer, the term of this patent is extended or adjusted under 35 U.S.C. 154(b) by 259 days.

(21) Appl. No.: 13/824,072

(22) PCT Filed: Oct. 6, 2011

(86) PCT No.: PCT/JP2011/073597
§ 371 (c)(1),
(2), (4) Date: Mar. 15, 2013

(87) PCT Pub. No.: WO2012/046880
PCT Pub. Date: Apr. 12, 2012

(65) Prior Publication Data
US 2013/0178658 A1    Jul. 11, 2013

(30) Foreign Application Priority Data

Oct. 8, 2010 (JP) ................... 2010-228023
Oct. 8, 2010 (JP) ................... 2010-228024
Apr. 28, 2011 (JP) ................... 2011-100451
Apr. 28, 2011 (JP) ................... 2011-100452

(51) Int. Cl.
*C07C 43/162* (2006.01)
*C07C 41/08* (2006.01)

(52) U.S. Cl.
CPC ............... *C07C 43/162* (2013.01); *C07C 41/08* (2013.01); *C07C 2102/42* (2013.01)

(58) Field of Classification Search
CPC .... C07C 43/162; C07C 41/08; C07C 2102/42
USPC ........................................................ 568/665
See application file for complete search history.

(56) References Cited

U.S. PATENT DOCUMENTS 6,245,485 B1 *  6/2001  Aoai et al. ................. 430/288.1
6,632,586 B1 * 10/2003  Aoai et al. ................. 430/287.1

FOREIGN PATENT DOCUMENTS

| JP | 2001-278829 A | 10/2001 |
| JP | 2009-242484 A | 10/2009 |
| JP | 2010-053087 A | 3/2010 |
| WO | WO-2010/035903 A1 | 4/2010 |

OTHER PUBLICATIONS

International Search Report, mailed Nov. 8, 2011.

* cited by examiner

*Primary Examiner* — Rosalynd Keys
(74) *Attorney, Agent, or Firm* — Fishman Stewart Yamaguchi PLLC

(57) ABSTRACT

A novel divinyl ether compound having the formula (I):

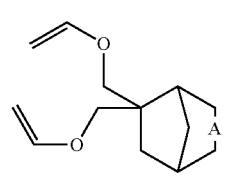

(I)

wherein A indicates a single bond or a double bond which is low in odor, low in volatility, and low in skin irritability, which have low toxicities, which are useful as a starting material for a polymer composition having excellent curability, adhesiveness and transmission in the ultraviolet light region, and further, having a special reactivity alone or with other compounds, and a process for producing the same.

2 Claims, 2 Drawing Sheets

DIVINYL-ETHER COMPOUND AND MANUFACTURING METHOD THEREFOR

TECHNICAL FIELD

The present invention relates to a novel divinyl ether compound, more particularly 2,2-bis[(ethenyloxy)methyl]bicyclo[2.2.1]heptane and 5,5-bis[(ethenyloxy)methyl]bicyclo[2.2.1]hept-2-ene, and a process for producing the same.

BACKGROUND ART

The divinyl ether compounds according to the present invention, specifically the 2,2-bis[(ethenyloxy)methyl]bicyclo[2.2.1]heptane (other name: 2,2-norbornanedimethanol divinyl ether) and 5,5-bis[(ethenyloxy)methyl]bicyclo[2.2.1]hept-2-ene (other name: 5-norbornene-2,2-dimethanol divinyl ether), have not been reported in the past and are believed to be novel compounds.

As a technical art relating to the divinyl ether compound according to the present invention, for example, there are the following Patent Literatures 1 and 2.

Patent Literature 1 describes a pentaerythritol acetal divinyl ether. This compound has an acetal structure, and therefore, easily hydrolyzes and differs from the divinyl ether compound according to the present invention in the point of stability to water.

Patent Literature 2 describes 1,3-adamantane dimethanol divinyl ether, but this compound differs from the divinyl ether compounds according to the present invention in the point of easy cyclization polymerization.

Patent Literature 1: Japanese Patent Publication No. 2009-242484A

Patent Literature 2: Japanese Patent Publication No. 2010-053087A

SUMMARY OF INVENTION

Problem to be Solved by the Invention

An object of the present invention is to provide novel divinyl ether compounds, specifically 2,2-bis[(ethenyloxy)methyl]bicyclo[2.2.1]heptane and 5,5-bis[(ethenyloxy)methyl]bicyclo[2.2.1]hept-2-ene, and a process for producing the same.

The novel divinyl ether compounds according to the present invention, specifically the 2,2-bis[(ethenyloxy)methyl]bicyclo[2.2.1]heptane and 5,5-bis[(ethenyloxy)methyl]bicyclo[2.2.1]hept-2-ene, are excellent in curability, adhesiveness, transmission of ultraviolet light, and stiffness, and therefore, are useful as a starting material for polymer composition, cross-linking agent, and various synthesis reagents. Accordingly, the novel divinyl ether compounds of the present invention can be utilized for applications such as inks, paints, resists, color filters, adhesives, printing materials, sealants, image-forming agents, etc.

Means for Solving Problem

In accordance with the present invention, there is provided a novel divinyl ether compound having the formula (I):

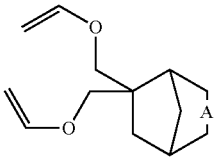

wherein, A indicates a single bond or a double bond.

In accordance with the production process of the present invention, it is possible to produce a novel divinyl ether compound of the formula (I):

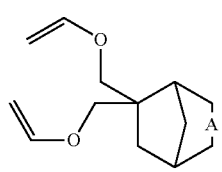

wherein, A indicates a single bond or a double bond specifically 2,2-bis[(ethenyloxy)methyl]bicyclo[2.2.1]heptane of the formula (I') or 5,5-bis[(ethenyloxy)methyl]bicyclo[2.2.1]hept-2-ene of the formula (I''):

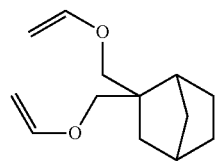

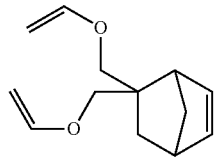

by reacting 2,2-norbornanedimethanol or 5-norbornene-2,2-dimethanol having the formula (II)

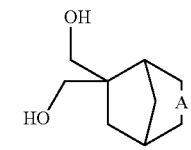

wherein, A indicates a single bond or a double bond with acetylene in the presence of an alkaline compound catalyst in an aprotic polar solvent.

Effects of Invention

The novel divinyl ether compound according to the present invention is low in odor, low in volatility, and low in skin irritability, has a low toxicity, and, further, can be expected to offer properties useful as starting materials for polymer compositions excellent in curability, adhesiveness, and transmission of ultraviolet light. Furthermore, the novel divinyl ether compound having the formula (I) of the present invention have the features of having two vinyl ether groups, which have special reactivity alone or with other compounds at specific positions.

DESCRIPTION OF EMBODIMENTS

Figure 1:
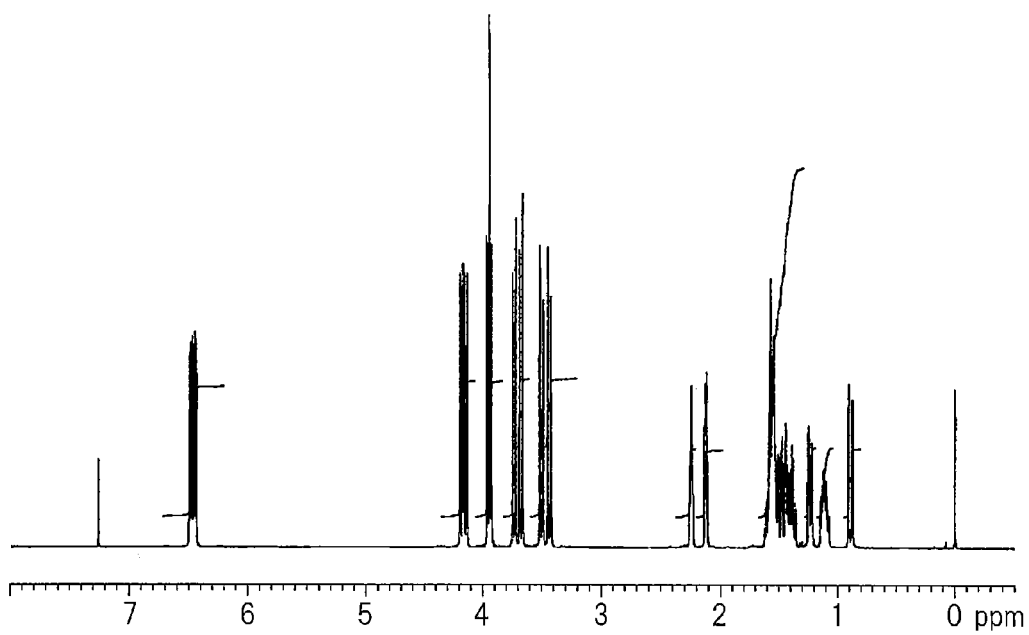
FIG. 1 is an $^1$H-NMR chart of 2,2-bis[(ethenyloxy)methyl]bicyclo[2.2.1]heptane

The present invention will now be described in detail.

According to the present invention, the divinyl ether compound (I) according to the present invention can be synthesized according to the following reaction formula:

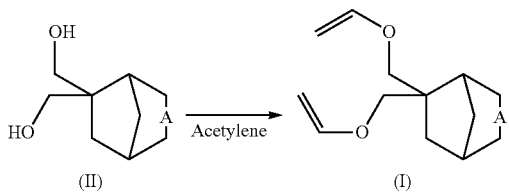

wherein A indicates a single bond or a double bond.

According to the first aspect of the present invention, 2,2-bis[(ethenyloxy)methyl]bicyclo[2.2.1]heptane (I') can be synthesized in the presence of an alkaline compound catalyst in an aprotic solvent according to the following reaction formula:

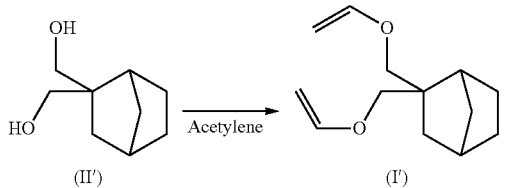

According to the second aspect of the present invention, 5,5-bis[(ethenyloxy)methyl]bicyclo[2.2.1]hept-2-ene(I") can be synthesized in the presence of an alkaline compound catalyst in an aprotic solvent according to the following reaction formula:

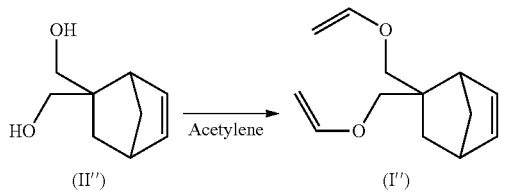

As a specific method of synthesis of the divinyl ether compound (I) in the present invention, for example, the following method may be mentioned:

To a reaction vessel such as a stainless steel (SUS) pressure-resistant reaction vessel, as a solvent an aprotic polar solvent such as at least one aprotic solvent selected from dimethylsulfoxide, N-methylpyrrolidone, N,N'-dimethylethyleneurea, N,N'-dimethylpropyleneurea, N,N'-diethylethyleneurea, N,N'-diisopropylethyleneurea, N,N,N',N',N",N"-hexamethylphosphoric acid triamide, 1,3,4-trimethyl-2-imidazolidinone, diethyleneglycol dimethyl ether, triethyleneglycol dimethyl ether, tetraethyleneglycol dimethyl ether, polyethyleneglycol dimethyl ether, etc., is charged, then the starting material compound, i.e., 2,2-norbornanedimethanol or 5-norbornene-2,2-dimethanol is fed and, as a reaction catalyst, for example, an alkaline compound such as, potassium hydroxide, sodium hydroxide, or another alkali metal hydroxide is added. At this time, the amount of the aprotic polar solvent to be used is not particularly limited, but the amount of the aprotic polar solvent to be used is preferably 100 to 1,000 parts by mass, more preferably 200 to 700 parts by mass, based upon 100 parts by mass of 2,2-norbornanedimethanol or 5-norbornene-2,2-dimethanol. If the amount of the aprotic polar solvent to be used is less than 100 parts by mass based upon 100 parts by mass of 2,2-norbornanedimethanol or 5-norbornene-2,2-dimethanol, the selectivity of the reaction is liable to fall, and therefore, this is not preferable. On the other hand, if the amount of the aprotic polar solvent to be used is over 1000 parts by mass based upon 100 parts by mass of 2,2-norbornanedimethanol or 5-norbornene-2,2-dimethanol, the removal of the solvent after the end of the reaction is liable to become troublesome, and therefore, this is not preferable. Further, the amount of the reaction catalyst, i.e., alkaline compound is not particularly limited either, but the amount of the alkaline compound to be used is preferably at least 2 parts by mass, more preferably 4 to 50 parts by mass, based upon 100 parts by mass of 2,2-norbornanedimethanol or 5-norbornene-2,2-dimethanol.

Next, by using an inert gas such as nitrogen gas, helium gas, argon gas, the atmosphere inside of the reaction vessel is replaced, then while the reaction vessel, is sealed and acetylene is fed under pressure, the temperature is raised to cause a reaction, it is possible to produce a divinyl ether compound having the formula (I) of the present invention, specifically the 2,2-bis[(ethenyloxy)methyl]bicyclo[2.2.1]heptane having the formula (I') or the 5,5-bis[(ethenyloxy)methyl]bicyclo[2.2.1]hept-2-ene having the formula (I"). The atmosphere inside of the reaction vessel may be acetylene alone, but nitrogen, helium, argon, or another inert gas may also be used, together with the acetylene.

In the present invention, as a reaction condition when producing the divinyl ether compounds having the formula (I), for example, the pressure of the acetylene is preferably a gauge pressure of 0.01 MPa or more. From the viewpoint of the productivity, suppression of side reactions, and safety, the acetylene pressure is more preferably a gauge pressure of 0.15 MPa to 1.0 MPa. On the other hand, the reaction temperature is preferably 80 to 140° C. From the viewpoint of the reaction rate, 100° C. or more is preferable, while from the viewpoint of the economy and suppression of side reactions, 130° C. or less is preferable.

Note that, the starting materials which are used in the present invention, that is, the 2,2-norbornanedimethanol or 5-norbornene-2,2-dimethanol (II) having the formula (II), are known compounds and can be produced by conventionally known processes. 2,2-norbornanedimethanol, for example, can be made by the process which is described in Synthesis Example 4 of Japanese unexamined Patent Publication No. 2005-29608A. Specifically, it can be produced from the 5-norbornene-2,2-dimethanol which is commercially available from Tokyo Kasei Industry Co., Ltd. under the product name "5-norbornene-2,2-dimethanol".

The divinyl ether compounds having the formula (I) according to the present invention may be polymerized alone or may be copolymerized with other monomers (e.g., n-butylvinylether) and can give polymers with high glass transition temperatures. The method of polymerization is not particularly limited, but, for example, a reaction in toluene using HCl/ZnCl$_2$ as a polymerization initiator, which is a conventional polymerizations method, may be used.

EXAMPLES

The present inventions will now be further illustrated by Examples, but the scope of the present invention is by no means limited to these Examples needless to say.

Preparation Example 1

Preparation of 2,2-norbornanedimethanol 138.18 g of 5-norbornene-2,2-dimethanol (commercially available from Tokyo Kasei Industry Co., Ltd.) was dissolved in 481.63 g of ethanol, and 6.92 g of 5% Pd—C was added, then a hydrogen balloon was attached and the mixture was stirred for 6 hours. The Pd—C was filtered off, then the reaction solution was concentrated and dried to thereby obtain 129.83 g of 2,2-norbornanedimethanol (purity by gas chromatography: 99.1%, yield: 92.9%).

Example 1

To an SUS pressure-resistant reaction vessel having a volume of 300 ml, provided with a stirrer, pressure gauge, thermometer, gas inlet tube, and gas purge line, 70.07 g of dimethylsulfoxide, 8.00 g (0.044 mol) of 2,2-norbornanedimethanol which was prepared in Preparation Example 1 and 1.52 g of potassium hydroxide having a purity of 95.0% (0.031 mol) were charged. Under stirring, nitrogen gas was run for about 60 minutes to replace the atmosphere in the inside of the vessel with nitrogen. Next, the reaction vessel was sealed and the inside of the vessel was filled with acetylene gas under a pressure of 0.18 MPa. Next, while holding the gauge pressure at 0.18 MPa, the temperature was gradually raised. The temperature inside of the reaction vessel was controlled so as to not exceed 90° C. and the reaction was continued for about 2 hours. During this time, acetylene gas was successively filled to hold the pressure inside of the reaction vessel at a constant 0.18 MPa. After the end of the reaction, the remaining acetylene gas was purged to obtain 95.90 g of the reaction solution. This reaction solution was analyzed by gas chromatography. As a result, the conversion of 2,2-norbornanedimethanol proceeded quantitatively and the selectivity of the desired 2,2-bis[(ethenyloxy)methyl]bicyclo[2.2.1]heptane was 99.2%.

Next, to the above reaction solution, 197 g of heptane and 190 g of distilled water were added. The mixture was stirred and filtered, then the top layer was drained off and the resultant product was treated with activated carbon and concentrated under reduced pressure. This concentrate was further distilled under reduced pressure (0.2 kPa) and 7.22 g of the fraction distilled off at 89° C. to 93° C. was collected. The fraction thus obtained was analyzed by NMR. As a result, it was 2,2-bis[(ethenyloxy)methyl]bicyclo[2.2.1]heptane having the following formula (purity by gas chromatography: 99.5%, yield: 79.3%).

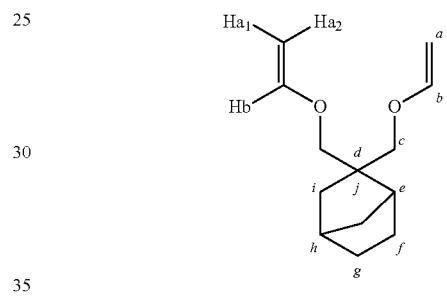

Figure 2:
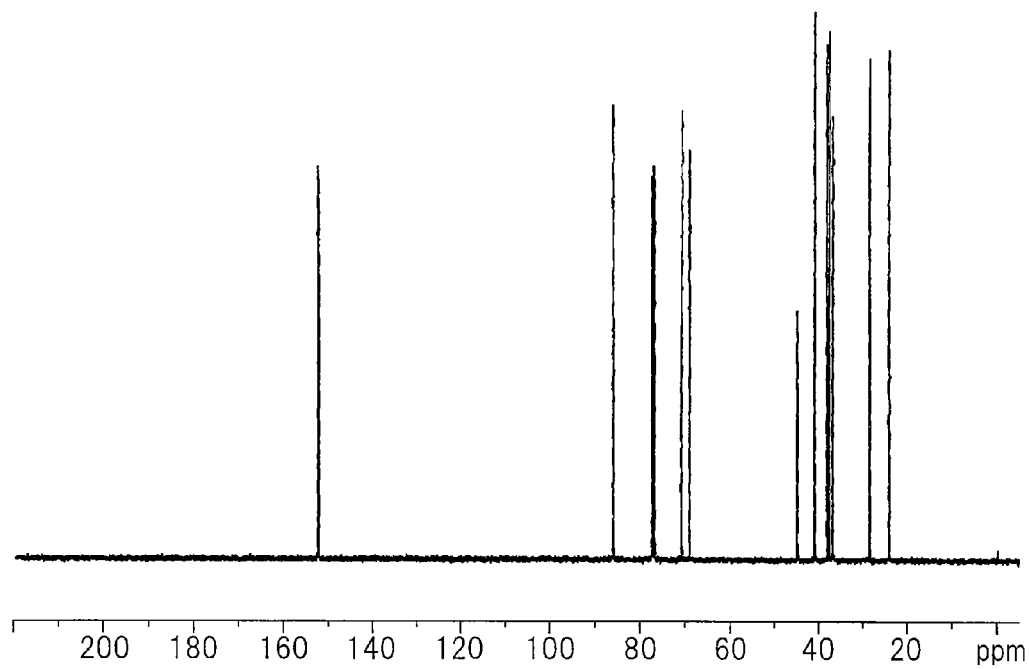
FIG. 2 is a $^{13}$C-NMR chart of 2,2-bis[(ethenyloxy)methyl]bicyclo[2.2.1]heptane

The characteristic absorption values of NMR analysis of the 2,2-bis[(ethenyloxy)methyl]bicyclo[2.2.1]heptanes thus obtained were as shown in Table I. Further, the $^1$H-NMR chart of the resultant 2,2-bis[(ethenyloxy)methyl]bicyclo[2.2.1]heptane is shown in FIG. 1, while the $^{13}$C-NMR chart is shown in FIG. 2.

TABLE I

| | $^1$HNMR (CDCl$_3$, TMS, 400 MHz) | | | | | $^{13}$CNMR (CDCl$_3$, TMS, 100 MHz) | | |
|---|---|---|---|---|---|---|---|---|
| | δ ppm | | | | | | δ ppm | |
| b | 6.47 | dd = 6.5, 14.5 Hz | 2H | CH$_2$=C$\underline{H}$—O | b | 152.3, 152.1 | | CH$_2$=$\underline{C}$H—O |
| a$_2$ | 4.17 | dd = 2.83, 14.5 Hz | 2H | C$\underline{H_2}$=CH—O | | | | |
| a$_1$ | 3.95 | dd = 2.83, 6.5 Hz | 2H | C$\underline{H_2}$=CH—O | a | 86.0, 85.9 | | $\underline{C}$H$_2$=CH—O |
| c | 3.73 | d = 10 Hz | 1H | C$\underline{H_2}$—O | | | | |
| c | 3.68 | d = 10 Hz | 1H | C$\underline{H_2}$—O | | | | |
| c | 3.50 | d = 10 Hz | 1H | C$\underline{H_2}$—O | | | | |
| c | 3.44 | d = 10 Hz | 1H | C$\underline{H_2}$—O | c | 70.6, 69.0 | | $\underline{C}$H$_2$—O |
| d | | | | | d | 44.8 | | $\underline{C}$ |
| e | 2.24 | t = 4 Hz | 1H | C$\underline{H}$ | e | 40.9 | | $\underline{C}$H |
| h | 2.13 | d = 4 Hz | 1H | C$\underline{H}$ | h | 38.3 | | $\underline{C}$H |
| fgij | 1.63-1.35 | m | 5H | C$\underline{H_2}$ | fgij | 37.7, 36.9, 28.6, 24.2 | | $\underline{C}$H$_2$ |
| i | 1.24 | dd = 2, 10 Hz | 1H | C$\underline{H_2}$ | | | | |
| f | 1.12 | m | 1H | C$\underline{H_2}$ | | | | |
| j | 0.89 | dd = 4, 12 Hz | 1H | C$\underline{H_2}$ | | | | |

Application Example 1

As the polymerization initiator and Lewis acid, HCl/ZnCl$_2$ were used. To a Schlenk flask, 4.0 ml of the 2,2-bis[(ethenyloxy)methyl]bicyclo[2.2.1]heptane which was obtained in Example 1 in a 9 mass % toluene solution, 0.5 ml of a 0.18% HCl solution and 0.5 ml of a ZnCl$_2$ solution were filled in that order by a syringe to start polymerization. The polymerization was performed in toluene at −30° C. with a monomer concentration of 0.30 mol/liter (containing tetralin as internal standard of gas chromatography), an HCl concentration of 5.0 mmol/liter, and a ZnCl$_2$ concentration of 2.0 mmol/liter. The polymerization reached a polymerization rate of 100% in 180 minutes. Methanol containing a small amount of ammonia water was added to the polymerization system to terminate the polymerization.

The resultant polymer was recovered by transferring the solution stopped in polymerization to a separating funnel, diluting it by methylene chloride, washing it by ion exchanged water three times, then removing the solvent from the organic layer by an evaporator and the drying in vacuo.

This polymer was further refined by decantation by methanol. The number average molecular weight (Mn) of the resultant polymer was 13,200, the molecular weight distribution (Mw/Mn) was 1.45, the glass transition temperature (Tg) was 165° C., and the thermal decomposition temperature (Td) was 337° C. Note that the measurement was performed using a differential scanning calorimeter (RIGAKU Thermo Plus DSC8230L) (below, same).

The divinyl ether homopolymer which was obtained in Application Example 1 was used for a starting material for paint use, whereupon it was low in odor, low in volatility, low in skin irritability, and low in toxicity. Further, it was high in glass transition temperature, and therefore, a paint film high in hardness and excellent in dryability and stain resistance was obtained.

Further, this was used for a starting material for photoresist use, whereupon it was low in odor, low in volatility, low in skin irritability, and low in toxicity. Further, it was high in glass transition temperature, and therefore, a resist which had an excellent strength was obtained.

Example 2

To an SUS pressure-resistant reaction vessel having a volume of 300 ml provided with a stirrer, pressure gauge, thermometer, gas inlet tube, and gas purge line, 70.07 g of dimethylsulfoxide, 7.00 g (0.038 mol) of 5-norbornene-2,2-dimethanol (commercially available from Tokyo Kasei Industry Co., Ltd.) and 1.30 g (0.027 mol) of potassium hydroxide having a purity of 95.0% were charged. Under stirring, nitrogen gas was run for about 60 minutes to replace the atmosphere in the inside of the vessel with nitrogen. Next, the reaction vessel was sealed and the inside of the vessel was filled with acetylene gas under a pressure of 0.18 MPa. Next, while holding the gauge pressure at 0.18 MPa, the temperature was gradually raised. The temperature inside of the reaction vessel was controlled so as to not exceed 90° C. and the reaction was continued for about 2 hours and 30 minutes. During this time, acetylene gas was successively filled to hold the pressure inside of the reaction vessel at a constant 0.18 MPa. After the end of the reaction, the remaining acetylene gas was purged to obtain 81.99 g of the reaction solution. This reaction solution was analyzed by gas chromatography. As a result, the conversion of 5-norbornene-2,2-dimethanol proceeded quantitatively and the selection rate of the desired 5,5-bis[(ethenyloxy)methyl]bicyclo[2.2.1]hept-2-ene was 99.9%.

Next, to the above reaction solution, 160 g of heptanes and 160 g of distilled water were added. The mixture was stirred and filtered, then the top layer was drained off and the resultant product was concentrated under reduced pressure. This concentrate was further distilled under reduced pressure (0.3 kPa) and 6.50 g of the fraction distilled off at 96° C. to 100° C. was collected. This resultant fraction was analyzed by NMR. As a result, it was 5,5-bis[(ethenyloxy)methyl]bicyclo[2.2.1]hept-2-ene of the following formula (purity by gas chromatography: 99.0%, yield: 81.5%).

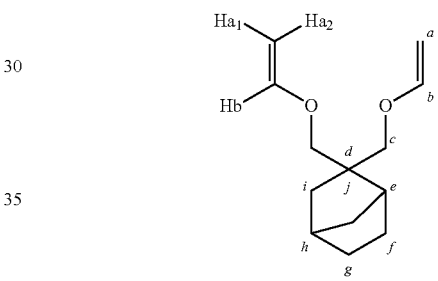

Figure 3:
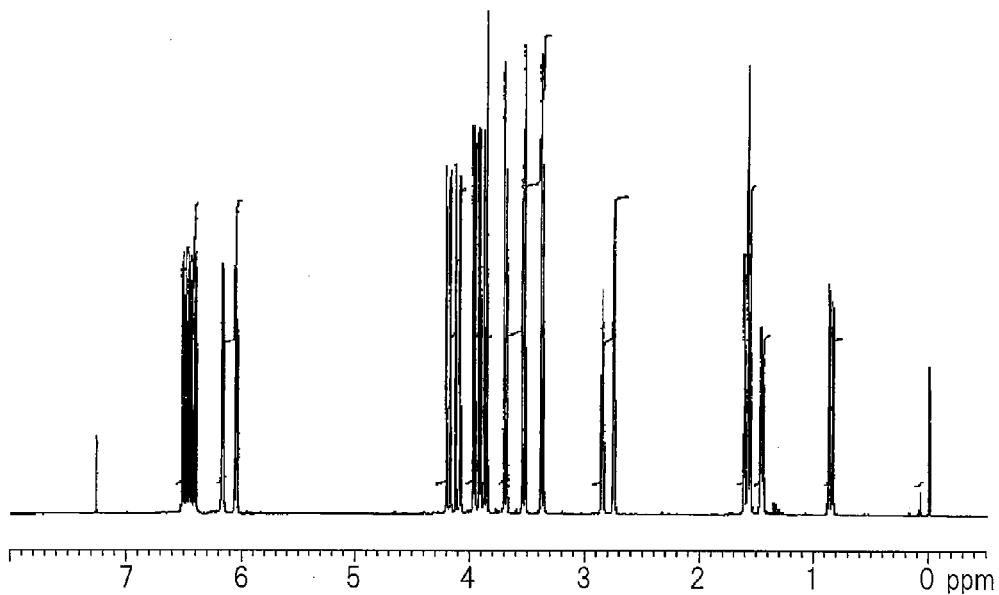
FIG. 3 is an $^1$H-NMR chart of 5,5-bis[(ethenyloxy)methyl]bicyclo[2.2.1]hept-2-ene
Figure 4:
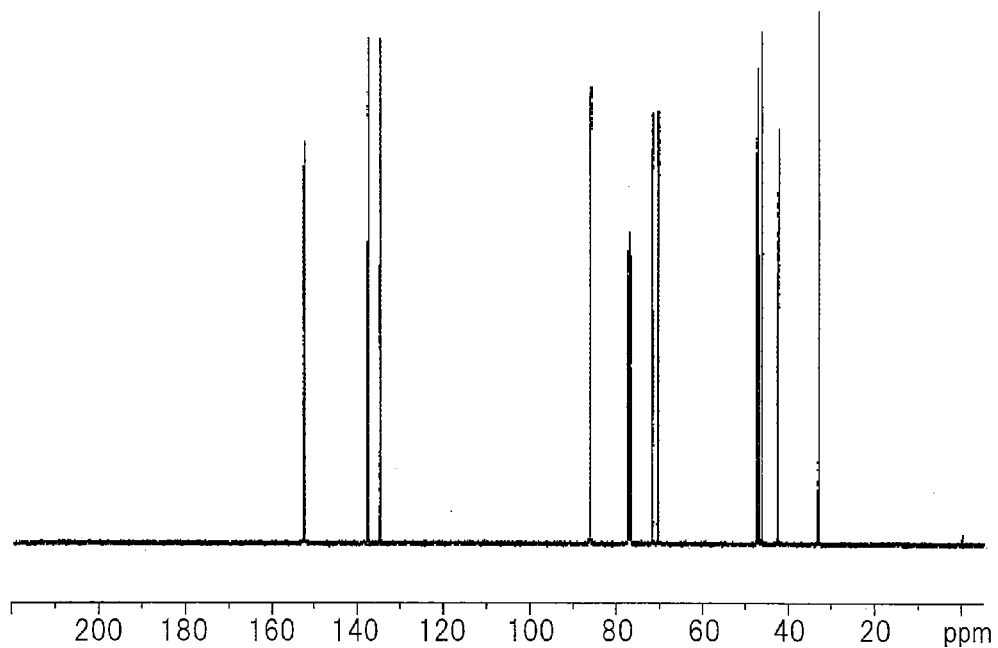
FIG. 4 is a $^{13}$C-NMR chart of 5,5-bis[(ethenyloxy)methyl]bicyclo[2.2.1]hept-2-ene

The characteristic absorption values of NMR analysis of the obtained 5,5-bis[(ethenyloxy)methyl]bicyclo[2.2.1]hept-2-ene are as shown in Table II. Further, the $^1$H-NMR chart of the obtained 5,5-bis[(ethenyloxy)methyl]bicyclo[2.2.1]hept-2-ene is shown in FIG. 3, while the $^{13}$C-NMR chart is shown in FIG. 4.

TABLE II

| | $^1$HNMR (CDCl$_3$, TMS, 400 MHz) | | | | | $^{13}$CNMR (CDCl$_3$, TMS, 100 MHz) | |
|---|---|---|---|---|---|---|---|
| | δ ppm | | | | | δ ppm | |
| b | 6.46 | dd = 7.5, 14 Hz | 2H | CH$_2$=C$\underline{H}$—O | b | 152.3, 152.1 | CH$_2$=$\underline{C}$H—O |
| g | 6.17 | dd = 3.4 Hz | 1H | C$\underline{H}$=CH | | | |
| f | 6.05 | dd = 4.4 Hz | 1H | C$\underline{H}$=CH | | | |
| a$_2$ | 4.14 | dd = 1.5, 14 Hz | 2H | C$\underline{H_2}$=CH—O | fg | 137.4, 134.5 | $\underline{C}$H=CH |
| a$_1$ | 3.94 | dd = 1.5, 7.5 Hz | 2H | C$\underline{H_2}$=CH—O | a | 86.1, 85.9 | $\underline{C}$H$_2$=CH—O |
| c | 3.86 | d = 8 Hz | 1H | C$\underline{H_2}$—O | | | |
| c | 3.69 | d = 8 Hz | 1H | C$\underline{H_2}$—O | | | |
| c | 3.53 | d = 8 Hz | 1H | C$\underline{H_2}$—O | | | |
| c | 3.37 | d = 8 Hz | 1H | C$\underline{H_2}$—O | c | 71.7, 70.3 | $\underline{C}$H$_2$—O |
| h | 2.86-2.82 | Broad | 1H | C$\underline{H}$ | h | 47.2 | $\underline{C}$H |
| e | 2.75 | d = 4 Hz | 1H | C$\underline{H}$ | e | 46.1 | $\underline{C}$H |
| d | | | | | d | 46.7 | $\underline{C}$ |
| j | 1.56 | dd = 4, 12 Hz | 2H | C$\underline{H_2}$ | | | |
| j | 1.45 | db = 8 Hz | 2H | C$\underline{H_2}$ | ij | 42.4, 32.9 | $\underline{C}$H$_2$ |
| i | 0.85 | dd = 1.8 Hz | 2H | C$\underline{H_2}$ | | | |
| i | 0.87-0.83 | dd = 1, 14 Hz | 2H | C$\underline{H_2}$ | | | |

Application Example 2

As the polymerization initiator and Lewis acid, HCl/ZnCl$_2$ were used. To a Schlenk flask, the 5,5-bis[(ethenyloxy)methyl]bicyclo[2.2.1]hept-2-ene which was obtained in Example 2 in 4.0 ml of a 9 mass % toluene solution, 0.5 ml of a 0.18% HCl solution and 0.5 ml of a ZnCl$_2$ solution were filled in that order by a syringe to start polymerization. The polymerization was performed in toluene at −30° C. with a monomer concentration of 0.30 mol/liter (containing tetralin as internal standard of gas chromatography), an HCl concentration of 5.0 mmol/liter, and a ZnCl$_2$ concentration of 2.0 mmol/liter. The polymerization reached a polymerization rate of 91% in 60 minutes. Methanol containing a small amount of ammonia water was added to the polymerization system to terminate the polymerization.

The polymer thus produced was recovered by transferring the solution stopped in polymerization to a separating funnel, diluting it by methylene chloride, washing it by ion exchanged water three times, then removing the solvent from the organic layer by an evaporator and the drying in vacuo.

This polymer was further refined by decantation by methanol. The number average molecular weight (Mn) of the obtained polymer was 12,900, the molecular weight distribution (Mw/Mn) was 1.92, the glass transition temperature (Tg) was 162° C., and the thermal decomposition temperature (Td) was 271° C.

The divinyl ether homopolymer which was obtained in Application Example 2 was used for a starting material for paint use, whereupon it was low in odor, low in volatility, low in skin irritability, and low in toxicity. Further, it was high in glass transition temperature, and therefore, a paint film high in hardness and excellent in dryability and stain resistance was obtained.

Further, this was used for a starting material for photoresist use, whereupon it was low in odor, low in volatility, low in skin irritability, and low in toxicity. Further, it was high in glass transition temperature, and therefore, a resist which had an excellent strength was obtained.

INDUSTRIAL APPLICABILITY

The novel divinyl ethers having the formula (I) according to the present invention were polymerized to obtain divinyl ether homopolymers, whereupon it was possible to obtain polymers exhibiting the excellent performances of high glass transition temperatures. Further, these polymers were excellent in curability, substrate adhesiveness, and transparency and, in addition, were excellent in heat resistance, so are useful for applications such as starting materials for ink use such as inks and paints and starting materials for electronic material use such as resists, color filters, adhesives, printing materials, sealants, and image-forming agents.

The invention claimed is:

1. A divinyl ether compound of the chemical name 5,5-bis[(ethenyloxy)methyl]bicyclo[2.2.1]hept-2-ene having the structural formula (I″):

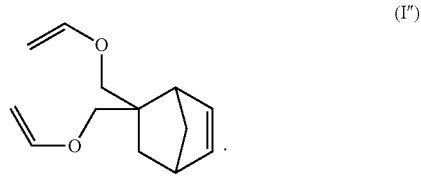

2. A process for producing a divinyl ether compound having the formula (I) comprising reacting 2,2-norbornanedimethanol or 5-norbornene-2,2-dimethanol having the formula (II)

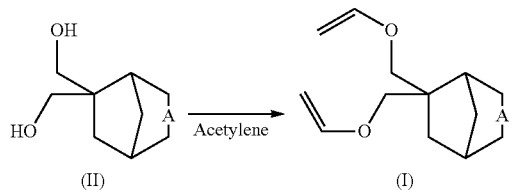

wherein A indicates a single bond or a double bond with acetylene in the presence of an alkaline compound catalyst in an aprotic polar solvent.

* * * * *